United States Patent [19]

Hammon et al.

[11] Patent Number: 5,728,272
[45] Date of Patent: Mar. 17, 1998

[54] SEPARATION BY RECTIFICATION OF UNSATURATED CARBOXYLIC ACIDS FROM SOLVENTS

[75] Inventors: Ulrich Hammon, Mannheim; Volker Schliephake, Schifferstadt; Wolfgang Pies, Frankenthal; Ulrich Rauh, Limburgerhof, all of Germany

[73] Assignee: BASF Aktiengesellschaft, Ludwigshafen, Germany

[21] Appl. No.: 696,193

[22] Filed: Aug. 13, 1996

[30] Foreign Application Priority Data

Sep. 28, 1995 [DE] Germany ............ 195 36 179.2

[51] Int. Cl.[6] .................. B01D 3/00; B01D 59/00
[52] U.S. Cl. ................. 203/8; 203/37; 203/59; 203/DIG. 21
[58] Field of Search ............... 203/DIG. 21, 8, 203/37, 36, 59

[56] References Cited

U.S. PATENT DOCUMENTS 3,157,693  11/1964  Wheeler et al. ............... 203/8
3,470,238  9/1969   Asano et al. ............ 203/DIG. 21
3,818,079  6/1974   Sato et al. .................... 203/8
3,893,895  7/1975   Dehnert et al. ............... 203/59

FOREIGN PATENT DOCUMENTS 0 648 732   4/1995   European Pat. Off. .
5-310636    5/1993   Japan .
7-64791     7/1995   Japan .

*Primary Examiner*—Nina Bhat
*Attorney, Agent, or Firm*—Oblon, Spivak, McClelland, Maier & Neustadt, P.C.

[57] ABSTRACT

In a process for the separation by rectification of unsaturated carboxylic acids from solvents in which the acids were absorbed after the synthesis reaction, the rectification is briefly interrupted and the rectification column is flushed with a basic solution. The interruption is carried out at regular time intervals. The basic solution used is an aqueous solution of alkali metal and/or alkaline earth metal hydroxide, preferably NaOH, KOH, $Ca(OH)_2$ or their anhydrous oxides; alkaline polar organic solvents as amines or amides can be used, too.

17 Claims, No Drawings

SEPARATION BY RECTIFICATION OF UNSATURATED CARBOXYLIC ACIDS FROM SOLVENTS

The present invention relates to a process for the separation by rectification of unsaturated carboxylic acids from solvents in which the acids were absorbed after the synthesis reaction.

Unsaturated carboxylic acids of the acrylic acid or methacrylic acid type are at present prepared industrially primarily by heterogeneously catalyzed gas-phase oxidation of the corresponding alkenes, alkanes or the unsaturated aldehydes. Various processes used at present differ primarily in the way the oxidation is conducted and in the process technology for separating off the secondary components unavoidably formed in the process (DE-A 19 62 431, DE-A 29 43 707). In the synthesis, the individual processes differ in whether the reaction gas is circulated and in the type of inert gas added. In the work-up, the difference lies primarily in whether the desired product which comes from the reactors as a hot gas is absorbed in a low-boiling or high-boiling solvent. All these processes have in common that at the end the desired product has to be separated by distillation from the absorbing solvent. This separation is generally carried out by distillation or rectification.

To avoid polymerization during the distillation or rectification, stabilizers such as phenothiazine (PTZ), hydroquinone methyl ether (MeHQ) or hydroquinone (HQ) are used. Nevertheless, polymer formation occurs in the rectification column after a relatively long period of operation and these force regular shutdown and laborious cleaning of the plant. This cleaning can be carried out mechanically or by thermal oxidation in a known manner. However, this is very time consuming.

It is an object of the present invention to provide a process by means of which the polymers can be removed in a simple and reliable manner and without requiring a great deal of time.

We have found that this object is achieved by the rectification being interrupted and the rectification column being flushed with a basic solution. The basic solution used is advantageously an aqueous solution of alkali metal and/or alkaline earth metal hydroxide, preferably NaOH, KOH, $Ca(OH)_2$ or their anhydrous oxides. The compounds dissolved in water here have a concentration of from 0.01 to 30% by weight, preferably from 0.5 to 10% by weight. According to an advantageous embodiment of the invention, an essentially neutral alkali metal or alkaline earth metal salt is added to the basic solution in a ratio of from >0:1 to 2:1 (weight ratio of neutral salt to hydroxide). Particularly suitable for this purpose are the sulfates, acetates, oxalates, carbonates, hydrogensulfates, hydrogencarbonates or other salts corresponding to the basic compounds. Such an addition enables the solvent behavior of the basic solution to be further improved.

According to a further embodiment of the present invention, alkaline polar organic solvents such as amines or amides, preferably acetamides, particularly preferably monoacetamide ($CH_3CONH_2$), can be used as solvents in place of alkaline aqueous solutions. Further solvents which can be used for this purpose are monomethylacetamide ($CH_3CON(CH_3)H$), dimethylacetamide ($CH_3CON(CH_3)_2$) and dimethylformamide ($HCON(CH_3)_2$).

The temperatures at which the flushing according to the present invention is carried out are determined by the boiling point of the solvents used, since the solvent action of all the abovementioned solvents increases with rising temperature. The optimum temperature for the aqueous systems of the alkali metal and alkaline earth metal hydroxides is from >80° C. to about 115° C. at atmospheric pressure, preferably from 90° C. to 110° C. For the amides described, the optimum use temperature is in each case from 10° to 1° C. below the boiling point of the respective substance.

The process of the present invention can be carried out either at regular time intervals or after a certain degree of deposit formation is determined. In each case, a shorter period of interruption of the distillation process is required and, in particular, a considerably simpler and more complete removal of the polymer deposits is achieved.

Further details and advantages of the invention may be found in the experimental examples described below.

Of course, the process of the present invention can be used quite generally in the separation by rectification of unsaturated carboxylic acids, for example also in the pure distillation of crude methacrylic acid to give pure methacrylic acid. It is found to be particularly advantageous to use the process of the present invention preventively, ie. at intervals, before visible deposit formation has occurred. In this way, deposit formation is in fact stopped right at the beginning.

The laboratory experiments gave the following results.

Experiment 1

(Reference Experiment, According to the Prior Art)

A Diphyl/acrylic acid mixture was distilled in a glass column (internal diameter 8 cm, 40 bubble cap trays). This mixture was taken from a production plant operating according to a process as described in DE 21 36 396.

The runback was stabilized with phenothiazine. After 238 hours, the column displayed backing up of liquid due to polymer formation. The column was shut down and first flushed with hot water for six hours. Result: the polymer was not removed and had to be removed subsequently by mechanical means. The total cleaning time was a full working day.

Experiment 2

(Flushing with Alkali According to the Present Invention)

The procedure was as for Experiment 1, backing up occurred after 212 hours. Flushing with a 5% strength by weight aqueous NaOH solution at 92° C. completely dissolved the polymer after 6 hours of flushing.

Experiment 3

(Flushing with Alkali/Sulfate According to the Present Invention)

The procedure was as for Experiment 2, backing up occurred after 254 hours. Flushing with an aqueous solution containing 5% by weight of NaOH and 5% by weight of $Na_2SO_4$ at 92° C. gave complete removal of the polymer after a flushing time of only 5 hours.

Experiment 4

(Flushing with Amide According to the Present Invention)

The procedure was as for Experiment 2, backing up occurred after 205 hours. Flushing with monomethylacetamide at 190° C. gave complete removal of the polymer after a flushing time of 6 hours.

Production Experiments

The knowledge gained in the laboratory was then used in an industrial plant. The experiments were carried out in an acrylic acid plant operating according to a process as described in DE 21 36 396. This process can be briefly described as follows:

heterogeneously catalyzed gas-phase oxidation of propylene and/or acrolein to give acrylic acid separation of the acrylic acid and a part of the secondary components from the reaction gas by countercurrent absorption using a high-boiling solvent separation of a first fraction of low-boiling and middle-boiling components by countercurrent desorption separation by distillation of the acrylic acid and the low-boiling and middle-boiling secondary components from the high-boiling solvent.

The solvent is recirculated to the absorption column.

The pure column arranged at the end of this work-up has a side offtake for the purified raw acrylic acid. To prevent occurrence of backing up due to polymer formation and achieve an overall very long operation time, the column was shut down for a short time after a running time of from 10 to 70 days, preferably from 20 to 50 days, for the purposes of cleaning according to the process of the present invention. This ensured very long, reliable operation of the column. The time at which the column was shut down was determined as a function of throughput and further parameters.

Flushing according to the present invention using a 10% strength by weight aqueous NaOH solution at 92° C. could be concluded in 8 hours.

Flushing using a 10% strength by weight aqueous NaOH solution to which 5% by weight of sodium sulfate (based on the NaOH solution) had been added and carried out at 92° C. could be completed even more quickly, requiring only 7 hours of flushing time. Comparative flushing using monomethylacetamide as solvent likewise required a flushing time of 7 hours at 92° C.

We claim:

1. A process for the separation of an unsaturated carboxylic acid from a composition comprising said unsaturated carboxylic acid and a solvent, which comprises separating said unsaturated carboxylic acid from said composition by rectification in a column with intermittent interruption of the rectification and flushing of the rectification column with a basic solution to clean the column.

2. A process as claimed in claim 1, wherein the interruption is carried out at regular time intervals.

3. A process as claimed in claim 1, wherein the basic solution comprises an hydroxide and a neutral alkali metal or alkaline earth metal salt in a weight ratio of the neutral salt to the hydroxide of from >0:1 to 2:1.

4. A process as claimed in claim 3, wherein said neutral salt is selected from the group consisting of sulfates, acetates, oxylates and carbonates.

5. A process as claimed in claim 1, wherein flushing is carried out at from 80° C. to 115° C., and at atmospheric pressure.

6. A process as claimed in claim 5, wherein flushing is carried out at from 90° C. to 110° C.

7. A process as claimed in claim 1, wherein the basic solution comprises an alkaline polar organic solvent.

8. A process as claimed in claim 7, wherein said alkaline polar organic solvent is selected from the group consisting of amines and amides.

9. A process as claimed in claim 7, wherein said alkaline polar organic solvent is an acetamide.

10. A process as claimed in claim 7, wherein said alkaline polar organic solvent is monoacetamide.

11. A process as claimed in claim 7, wherein said basic solution consists of said alkaline polar organic solvent.

12. A process as claimed in claim 1, wherein said basic solution is an aqueous solution of a base selected from the group consisting of alkali metal hydroxides and alkaline earth metal hydroxides.

13. A process as claimed in claim 12, wherein said base is dissolved in water at a concentration of from 0.01 to 30% by weight.

14. A process as claimed in claim 12, wherein said base is dissolved in water at a concentration of from 0.5 to 10% by weight.

15. A process as claimed in claim 1, wherein said basic solution is an aqueous solution of a base selected from the group consisting of NaOH, KOH, Ca(OH)$_2$ and their anhydrous oxides.

16. A process as claimed in claim 15, wherein said base is dissolved in water at a concentration of from 0.01 to 30% by weight.

17. A process as claimed in claim 15, wherein said base is dissolved in water at a concentration of from 0.5 to 10% by weight.

* * * * *